United States Patent [19]

Seper et al.

[11] Patent Number: 5,196,593

[45] Date of Patent: Mar. 23, 1993

[54] HALOGENATED TRIFLUOROMETHYLBENZENES

[75] Inventors: Karl W. Seper; James J. Maul; Henry C. Lin, all of Grand Island, N.Y.

[73] Assignee: Occidental Chemical Corporation, Niagara Falls, N.Y.

[21] Appl. No.: 264,729

[22] Filed: Oct. 31, 1988

[51] Int. Cl.$^5$ ............................................. C07C 211/45
[52] U.S. Cl. .................................................... 564/442
[58] Field of Search .......................... 71/116; 558/425; 562/493; 564/183, 442

[56] References Cited

U.S. PATENT DOCUMENTS

| | | | |
|---|---|---|---|
| 3,823,134 | 7/1974 | Houlihan | 564/183 |
| 4,093,446 | 6/1978 | Bayer | 558/424 |
| 4,581,361 | 4/1986 | Berlin et al. | 514/301 |
| 4,582,948 | 4/1986 | Tang et al. | 568/938 |
| 4,603,222 | 7/1986 | Tang et al. | 568/315 |

FOREIGN PATENT DOCUMENTS 0023392 2/1981 European Pat. Off. .

OTHER PUBLICATIONS

Feast, W. J., *J. Chem. Soc.* (C), 1971, pp. 1547–1549.

*Primary Examiner*—Joseph Paul Brust
*Assistant Examiner*—Jacqueline Haley
*Attorney, Agent, or Firm*—Wayne A. Jones; Arthur S. Cookfair

[57] ABSTRACT

Novel halogenated trifluoromethylbenzenes have the structural formula

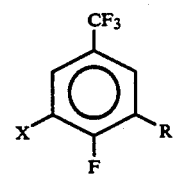

wherein X is halogen, preferably Cl, F or Br, and R is a group selected from the group consisting of —COOH, —C(O)NH$_2$ and —CN. These compounds are intermediates for pesticidal trifluoromethyl diphenyl ethers and are converted thereto by replacing the fluorine para to the trifluoromethyl with substituted phenoxy group in aromatic nucleophilic substitution.

A novel intermediate which is converted by reaction with cuprous cyanide and HONO to compound having the above structural formula where X is F and R is —CN is 2,3-difluoro-5-(trifluoromethyl)aniline and has the formula

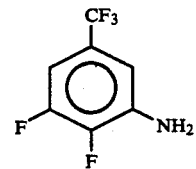

1 Claim, No Drawings

HALOGENATED TRIFLUOROMETHYLBENZENES

TECHNICAL FIELD

This invention is directed to novel halogenated trifluoromethylbenzenes useful as intermediates for the preparation of pesticidal trifluoromethyl diphenyl ethers and also for the preparation of each other.

BACKGROUND OF THE INVENTION

Pesticidal trifluoromethyl diphenyl ethers are known having the structural formula:

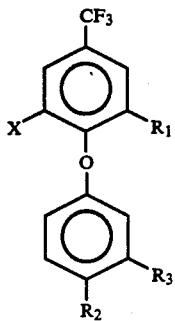

wherein X is halogen, $R_1$ is substituent which normally is chlorine, $R_2$ is, for example, —$NO_2$, and $R_3$ is, for example, —COOH, —C(O)NH$_2$ or —CN, wherein the ring with the trifluoromethyl substituent may be referred to as the "A" ring and the ring depicted with $R_2$ and $R_3$ may be referred to as the "B" ring.

While materials are known to readily produce said trifluoromethyl diphenyl ethers with —COOH, —C(O)NH$_2$ or —CN functionality in the "B" ring, heretofore there have been no intermediates for readily producing trifluoromethyl diphenyl ethers with —COOH, —C(O)NH$_2$ or —CN functionality at the $R_1$ position in the "A" ring.

SUMMARY OF THE INVENTION

It has been discovered herein that novel intermediates for readily producing pesticidal trifluoromethyl diphenyl ethers with —COOH, —C(O)NH$_2$ or —CN functionality in the "A" ring are halogenated trifluoromethylbenzenes having the structural formula

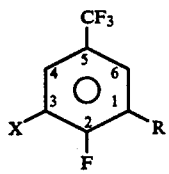

wherein X is halogen and R is a group selected from the group consisting of —COOH, —C(O)NH$_2$ or —CN. These novel intermediates are readily converted to pesticidal trifluoromethyl diphenyl ethers by replacing the fluorine which is para to the trifluoromethyl with substituted phenoxy group in an aromatic nucleophilic substitution.

DETAILED DESCRIPTION

The compounds of the structural formula (I) preferably contain X which is Cl, F or Br.

Thus preferred compounds herein are as follows: (1) compound having the structural formula (I) wherein X is Cl and R is —COOH, i.e., 3-chloro-2-fluoro-5-(trifluoromethyl)benzoic acid; (2) compound having the structural formula (I) wherein X is Cl and R is —C(O)NH$_2$, i.e., 3-chloro-2-fluoro-5-(trifluoromethyl) benzamide; (3) compound having the structural formula (I) wherein X is Cl and R is —CN, i.e., 3-chloro-2-fluoro-5-(trifluoromethyl)benzonitrile; (4) compound having the structural formula (I) wherein X is F and R is —COOH, i.e., 2,3-difluoro-5-(trifluoromethyl)benzoic acid; (5) compound having the structural formula (I) wherein X is F and R is —C(O)NH$_2$, i.e., 2,3-difluoro-5-(trifluoromethyl)benzamide; (6) compound having the structural formula (I) wherein X is F and R is —CN, i.e., 2,3-difluoro-5-(trifluoromethyl)benzonitrile; (7) compound having the structural formula (I) wherein X is Br and R is —COOH, i.e., 3-bromo-2-fluoro-5-(trifluoromethyl)benzoic acid; (8) compound having the structural formula (I) wherein X is Br and R is —C(O)NH$_2$, i.e., 3-bromo-2-fluoro-5-(trifluoromethyl)benzamide; and (9) compound having the formula (I) wherein X is Br and R is —CN, i.e., 3-bromo-2-fluoro-5-(trifluoromethyl)benzonitrile.

The novel intermediates herein are readily prepared starting with the appropriate 2-fluoro-5-(trifluoromethyl) benzene e.g., 1,3-dichloro-2-fluoro-5-(trifluoromethyl)benzene, and 1-chloro-2,3-difluoro-5-(trifluoromethyl)benzene, and 1,3-dibromo-2-fluoro-5-(trifluromethyl)benzene. These are available commercially or can be made, for example, as described in Cartwright, et al U.S. Pat. No. 4,384,135. Furthermore, the preparation of 1,3-dibromo-2-fluoro-5-(trifluoromethyl)benzene is described in columns 11 and 12 of Perrior et al U.S. Pat. No. 4,725,607.

Furthermore, the 2,3-difluoro intermediates herein are readily prepared by starting with 1,3-dinitro-2-chloro-5-(trifluoromethyl)benzene which is commercially available and is assigned CAS #109919-28-0.

The compounds (1), (4) and (7) above, i.e., 3-chloro-2-fluoro-5-(trifluoromethyl)benzoic acid and 2,3-difluoro-5-(trifluoromethyl)benzoic acid and 3-bromo-2-fluoro-5-(trifluoromethyl)benzoic acid are readily prepared by respectively carboxylating 1,3-dichloro-2-fluoro-5-(trifluoromethyl)benzene, 1-chloro-2,3-difluoro-5-(trifluoromethyl)benzene and 1,3-dibromo-2-fluoro-5-(trifluoromethyl)benzene at the 1-position, e.g., by reacting with an equimolar amount or slight excess of t-butyllithium and an excess of dry ice (at −78° C.) in diethyl ether/pentane and isolating by allowing the reaction mixture to warm to room temperature, acidifying with HCl, filtering to recover solid product, and drying.

The compounds (2), (5) and (8) above, i.e., 3-chloro-2-fluoro-5-(trifluoromethyl)benzamide, 2,3-difluoro-5-(trifluoromethyl)benzamide and 3-bromo-2-fluoro-5-(trifluoromethyl)benzamide are readily prepared by amidation of the corresponding acids, i.e., by amidation of compounds (1), (4) and (7) respectively, e.g., by reacting with a molar excess of thionyl chloride in dimethylformamide followed by adding the resulting reaction mixture to at least two equivalents of ice cold ammonium hydroxide and cooling to 0° C. and isolating by filtering to recover solid product, then washing and drying.

The compounds (3), (6) and (9) above, i.e., 3-chloro-2-fluoro-5-(trifluoromethyl)benzonitrile, 2,3-difluoro-5-(trifluoromethyl)benzonitrile and 3-bromo-2-fluoro-5-

(trifluoromethyl)benzonitrile are readily prepared by dehydrating the corresponding amides, i.e., by dehydrating compounds (2), (5) and (8) respectively, e.g., by reacting with an excess of thionyl chloride in the presence of a catalytic amount of dimethylformamide at 0° C. followed by diluting with pentane, neutralizing with saturated potassium carbonate solution, filtering the pentane solution and then drying and distilling.

As indicated above, an alternate route to compounds (4), (5) and (6) involves starting with 1,3-dinitro-2-chloro-5-(trifluoromethyl)benzene. In such route, this starting material is converted to 2,3-difluoro-5-(trifluoromethyl)nitrobenzene by substituting F for the 2-chloro and 3-nitro, and this, in turn, is reduced to 2,3-difluoro-5-(trifluoromethyl)aniline, a novel compound, which in turn is converted to 2,3-difluoro-5-(trifluoromethyl)benzonitrile, i.e., compound (6). Compound (6) is readily hydrolyzed to 2,3-difluoro-5-(trifluoromethyl)benzoic acid, i.e., compound (4) which is readily converted to 2,3-difluoro-5-(trifluoromethyl)benzamide, i.e., compound (5) as described above. The conversion of 1,3-dinitro-2-chloro-5-(trifluoromethyl)benzene to 2,3-difluoro-5-(trifluoromethyl) nitrobenzene is readily carried out by reacting with a stoichiometric excess of anhydrous KF in dimethylformamide at 140° to 145° C. The 2,3-difluoro-5-(trifluoromethyl)nitrobenzene is converted to 2,3-difluoro-5-(trifluoromethyl)aniline by heating with iron powder in aqueous HCl. The 2,3-difluoro-5-(trifluoromethyl)aniline is converted to 2,3-difluoro-5-(trifluoromethyl)benzonitrile, i.e., compound (6), by forming a diazonium solution by admixing the aniline with aqueous HCl, then adding sodium nitrite and then neutralizing with dry sodium carbonate, forming a cuprous cyanide solution, then adding the cold neutralized diazonium solution to cuprous cyanide solution admixed with toluene. The 2,3-difluoro-5-(trifluoromethyl)benzonitrile, i.e., compound (6) can be converted to 2,3-difluoro-5-(trifluoromethyl)benzoic acid, i.e., compound (4), by adding compound (6) to aqueous NaOH, and then heating at 95°-99° C.

For conversion to pesticidal trifluoromethyl diphenyl ethers, the compounds herein are reacted with the appropriate phenoxide salt which is preferably prepared in situ by reaction in an aprotic solvent in the presence of alkali metal carbonate, or excess of preferably anhydrous potassium carbonate.

To obtain pesticidal trifluoromethyl diphenyl ethers where 4'-nitrophenoxy is substituted for F para to trifluoromethyl in the compounds herein, p-nitrophenol can be reacted with compound herein in aprotic solvent, for example, dimethylsulfoxide, in the presence of an equimolar amount of anhydrous potassium carbonate at a temperature, for example, ranging from ambient to 180° C. for 2 to 100 hours or more. The product can be purified by pouring into an excess of dilute hydrochloric acid, filtering, and dissolving, washing and drying.

As indicated above, the intermediate, 2,3-difluoro-5-(trifluoromethyl)aniline is a novel compound. It has the structural formula (I) where X is F and R is —NH₂, i.e.,

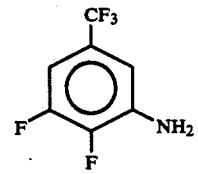

It has a boiling point of approximately 190° C.

The invention is illustrated in the specific examples which follow:

EXAMPLE I

3-Chloro-2-fluoro-5-(trifluoromethyl)benzoic acid is prepared as follows:

To a dry, nitrogen purged 250 mL 3 necked flask fitted with a low temperature thermometer, rubber septa and a nitrogen inlet was added 100 mL of a 70:30 mixture of dry diethyl ether and pentane followed by 10.0 g (43 mmol) of 1,3-dichloro-2-fluoro-5-(trifluoromethyl)benzene. To this solution at −78° C. was added dropwise 30 mL (45 mmol) of 1.7N solution of tertiary butyl lithium in pentane. After stirring at −78° C. for 0.5 hours, the contents of the flask were transferred via cannula to an Erlenmeyer flask containing ca. 10 g (250 mmol) of solid carbon dioxide. The contents of the Erlenmeyer flask were allowed to warm to room temperature, made acidic by dropwise addition of 6N HCl, filtered and air dried. Yield, 8.5 g (82%) of 3-chloro-2-fluoro-5-(trifluoromethyl)benzoic acid.

EXAMPLE II

3-Chloro-2-fluoro-5-(trifluoromethyl)benzamide was prepared as follows:

Thionyl chloride, 6.0 g (50 mmol) was added to a solution of 4.0 g (16 mmol) 3-chloro-2-fluoro-5-(trifluoromethyl) benzoic acid in 10 mL dimethylformamide. The reaction mixture was heated to 75° C. for 2 hours, cooled to room temperature and carefully added to 25 mL of ice cold ammonium hydroxide. The mixture was cooled to 0° C. and the solid product filtered, washed with water and dried to yield 3.96 g (99%) of 3-chloro-2-fluoro-5-(trifluoromethyl)benzamide.

EXAMPLE III

3-Chloro-2-fluoro-5-(trifluoromethyl)benzonitrile was prepared as follows:

Thionyl chloride, 6.0 g (50 mmol) was added to a slurry of 4.0 g (16 mmol) 3-chloro-2-fluoro-5-(trifluoromethyl) benzamide and 15 mL dimethylformamide at 0° C. After stirring for one hour the reaction mixture was diluted with 25 mL pentane and neutralized by dropwise addition of a saturated potassium carbonate solution and filtered. The pentane solution was dried and distilled to yield 3-chloro-2-fluoro-5-(trifluoromethyl) benzonitrile in 71% yield, bp 75°-85° C./20 mm Hg.

EXAMPLE IV 2,3-Difluoro-5-(trifluoromethyl)aniline was prepared as follows:

1,3-Dinitro-2-chloro-5-(trifluoromethyl)benzene was converted to 2,3-difluoro-5-(trifluoromethyl)nitrobenzene as follows: 1,3-Dinitro-2-chloro-5-(trifluoromethyl)benzene (100 g, 0.37 moles), 100 g of dimethylformamide and 129 g (2.22 moles) of anhydrous potassium fluoride were heated at 140° to 145° C. for 4.3 hours and then, after cooling, the reaction mixture was extracted with methylene chloride. The methylene chloride was distilled off and the product was redissolved in diethyl ether. The ether extracts were washed with water, dried over magnesium sulfate and distilled, to yield the desired product, bp 85°-97°/25 Torr.

25 g (0.11 moles) of 2,3-difluoro-5-(trifluoromethyl) nitrobenzene, 30 g of iron powder, 75 ml of water and 0.5 mol of conc. HCl are heated at reflux for 30 minutes. A second portion of conc. HCl is added and the mixture is again heated at reflux for 30 minutes. Finally 1.0 ml of conc. HCl is added and the reaction heated at reflux for 2 hours. 2 ml of 12N sodium hydroxide is added and the reaction mixture is steam distilled. The distillate is extracted with ethyl ether dried over magnesium sulfate and vacuum distilled, to yield the desired product, bp approximately 190° C.

EXAMPLE V 2,3-Difluoro-5-(trifluoromethyl)benzonitrile is prepared as follows:

A cuprous cyanide solution is prepared as follows: Cuprous chloride (24.75 g, 0.25 moles) is suspended in 150 ml of water. Sodium cyanide (32.5 g, 0.66 moles) is added, whereupon the cuprous chloride enters into solution (exothermic). The mixture is then cooled to 0° to 5° C. until used below.

A diazonium solution is prepared as follows: 2,3-Difluoro-5-(trifluoromethyl)aniline (45.5 g, 0.2 moles) is mixed with 50 ml of 28% hydrochloric acid and about 40 grams of cracked ice to bring the temperature of the mixture to 0° C. A solution of 14 g (0.203 moles) of sodium nitrite in 40 cc of water is added with stirring to the resulting suspension or aromatic amine hydrochloride, the temperature being kept at 0°-5° C. by the addition of cracked ice. The mixture is cautiously neutralized by adding dry sodium carbonate with constant stirring, using litmus paper to determine the end-point.

To the cuprous cyanide solution (0° C.) is added 50 ml of toluene. To this mixture is slowly added the cold neutralized diazonium solution. During this addition vigorous stirring is maintained. When the addition is complete, stirring is continued for an additional 30 minutes at 0° C. and then for 2 hours as the reaction temperature is allowed to raise to room temperature and finally at 50° C. for 30 minutes. The upper oily layer is transferred to a distillation flask (50 ml of water added) and steam distilled. The organic layer of the distillate is distilled to yield the desired nitrile, bp 65°-70° C./20 Torr.

EXAMPLE VI 2,3-Difluoro-5-(trifluoromethyl)benzoic acid is prepared as follows:

2,3-Difluoro-5-(trifluoromethyl)benzonitrile (60.03 g, 0.29 moles) is added to a solution of 17.5 g (0.43 moles) of sodium hydroxide in 158 ml of water. The mixture is heated to 97° C. during 1 hour and then heating is continued for an additional 2 hours. The mixture is acidified and the solid acid filtered off and air dried to yield 2,3-difluoro-5-(trifluoromethyl)benzoic acid, m.p. 94°-96° C.

EXAMPLE VII 2,3-Difluoro-5-(trifluoromethyl) benzoic acid is prepared as follows:

To a dry, nitrogen purged 250 mL 3 necked flask fitted with a low temperature thermometer, rubber septa and an nitrogen inlet is added 100 mL of 70:30 mixture of dry diethyl ether and pentane followed by 4.0 g (18 mmol) of 1-chloro-2,3-difluoro-5-(trifluoromethyl)benzene. To this solution at −78° C. is added dropwise 10 mL (18 mmol) of a 1.7N solution of tertiary butyllithium in pentane. After stirring at −78° C. for 0.5 hours the contents of the flask is transferred via cannula to an Erlenmeyer flask containing ca. 10 g (250 mmol) of solid carbon dioxide. The contents of the Erlenmeyer flask is allowed to warm to room temperature, made acidic by dropwise addition of 6N HCl, filtered and air dried to yield of 2,3-difluoro-5-(trifluoromethyl)benzoic acid melting at 94°-96° C.

EXAMPLE VIII 2,3-Difluoro-5-(trifluoromethyl) benzamide was prepared as follows:

Thionyl chloride, 6.0 g (50 mmol) was added to a solution of 3.50 g (15 mmol) 2,3-difluoro-5-(trifluoromethyl) benzoic acid in 10 mL dimethylformamide. The reaction mixture was heated to 75° C. for 2 hours, cooled to room temperature and carefully added to 25 mL of ice cold ammonium hydroxide. The mixture was cooled to 0° C. and the solid product filtered, washed with water and dried to yield 3.00 g (86%) of 2,3-difluoro-5-(trifluoromethyl)benzamide m.p. 128°-130° C.

EXAMPLE IX 2,3-Difluoro-5-(trifluoromethyl)benzonitrile was prepared as follows:

Thionyl chloride, 6.0 g (50 mmol) was added to a slurry of 4.0 g (18 mmol) 2,3-difluoro-5-(trifluoromethyl)benzamide and 15 mL dimethylformamide at 0° C. After stirring for 1 hour, the reaction mixture was diluted with 25 mL pentane and neutralized by dropwise addition of a saturated potassium carbonate solution and filtered. The pentane solution was dried and distilled to yield 2,3-difluoro-5-(trifluoromethyl) benzonitrile in 56% yield, bp 65°-70° C./20 mm Hg.

EXAMPLE X

When in Example I, an equimolar amount of 1,3-dibromo-2-fluoro-5-(trifluoromethyl)benzene is substituted for the 1,3-dichloro-2-fluoro-5-(trifluoromethyl)-benzene, 3-bromo-2-fluoro-5-(trifluoromethyl)benzoic acid is prepared.

EXAMPLE XI

When in Example II, an equimolar amount of 3-bromo-2-fluoro-5-(trifluoromethyl)benzoic acid is substituted for the 3-chloro-2-fluoro-5-(trifluoromethyl)-benzoic acid, 3-bromo-2-fluoro-5-(trifluoromethyl)benzamide is prepared.

EXAMPLE XII

When in Example III, an equimolar amount of 3-bromo-2-fluoro-5-(trifluoromethyl)benzamide is substituted for the 3-chloro-2-fluoro-5-(trifluoromethyl)benzamide, 3-bromo-2-fluoro-4-(trifluoromethyl)benzonitrile is prepared.

EXAMPLE XIII

Conversion to Pesticidal Trifluoromethyl Diphenyl Ether

3-Chloro-2-fluoro-5-(trifluoromethyl)benzoic acid and an equimolar amount of p-nitrophenol are stirred with an equimolar amount of anhydrous potassium carbonate in dimethylsulfoxide at 110° C. for 24 hours and then left overnight at room temperature. The mixture is then poured into dilute hydrochloric acid and the solid is recovered and purified by dissolving, washing and drying to give 4'-nitrophenoxy ether at the 2-position of 3-chloro-5-(trifluoromethyl)benzoic acid.

Corresponding pesticidal trifluoromethyl diphenyl ethers are also obtained when the compounds of Examples II, III, V, and VII–XII are substituted in equimolar amount for the 3-chloro-2-fluoro-5-(trifluoromethyl)-benzoic acid above.

Variations will be evident to those skilled in the art. Therefore, the scope of the invention is intended to be defined by the claims:

What is claimed is

1. Halogenated trifluoromethylbenzene having the structural formula:

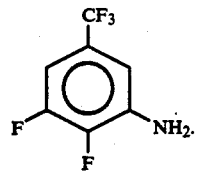

* * * * *